United States Patent
Bonfiglio

(10) Patent No.: US 10,467,380 B2
(45) Date of Patent: Nov. 5, 2019

(54) DEVICE AND SYSTEM TAILORED TO PROVIDE HEALTHCARE CONTENT, INFORMATION AND COMMUNICATION

(71) Applicant: TracFone Wireless, Inc., Miami, FL (US)

(72) Inventor: Nicholas Bonfiglio, Miami, FL (US)

(73) Assignee: Tracfone Wireless, Inc., Miami, FL (US)

( * ) Notice: Subject to any disclaimer, the term of this patent is extended or adjusted under 35 U.S.C. 154(b) by 714 days.

(21) Appl. No.: 14/605,450

(22) Filed: Jan. 26, 2015

(65) Prior Publication Data
US 2015/0213216 A1 Jul. 30, 2015

Related U.S. Application Data

(60) Provisional application No. 61/931,257, filed on Jan. 24, 2014.

(51) Int. Cl.
*G06Q 50/00* (2012.01)
*G06F 19/00* (2018.01)
(Continued)

(52) U.S. Cl.
CPC ..... *G06F 19/3418* (2013.01); *H04M 15/8083* (2013.01)

(58) Field of Classification Search
CPC ........ G06Q 50/22; G06Q 50/24; G06Q 40/08; G06Q 10/10; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06F 19/322; A61N 1/08; G16H 10/10; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50;
(Continued)

(56) References Cited

U.S. PATENT DOCUMENTS

2009/0204434 A1* 8/2009 Breazeale, Jr. ........ G06F 19/328
705/3

OTHER PUBLICATIONS

Brian Dolan, "Medagate's Medicaid members get Lifeline phones," 4 pages, Aug. 15, 2011, Mobihealth News, Online at http://www.mobihealthnews.com/12557/medagates-medicaid-members-get-lifeline-phones.†

* cited by examiner
† cited by third party

*Primary Examiner* — Tran N Nguyen
(74) *Attorney, Agent, or Firm* — Baker & Hostetler LLP

(57) ABSTRACT

The application is directed to a method and system for improving communication between a client and health care provider via an electronic device. The method includes the steps of displaying a communication from a health care provider on a display of the device. Next it is determined whether the communication was received by a predetermined health care provider. Further, a predetermined deduction rate is applied to the received communication on the device from the predetermined health care provider.

18 Claims, 6 Drawing Sheets

(51) Int. Cl.
*G06Q 10/00* (2012.01)
*H04M 15/00* (2006.01)

(58) Field of Classification Search
CPC ........ G16H 50/70; G16H 50/80; G16H 70/00; G16H 70/20; G16H 70/14; G16H 70/60; G16H 80/00
See application file for complete search history.

DEVICE AND SYSTEM TAILORED TO PROVIDE HEALTHCARE CONTENT, INFORMATION AND COMMUNICATION

CROSS REFERENCE TO PRIOR APPLICATIONS

This application claims the benefit from U.S. Provisional Application No. 61/931,257 filed on Jan. 24, 2014, which is hereby incorporated by reference for all purposes as if fully set forth herein.

BACKGROUND OF THE DISCLOSURE

1. Field of the Disclosure

This application generally relates to methods, systems, and software applications for providing healthcare content and information and improving communication between healthcare providers and clients on wireless devices. More particularly, this application relates to methods, systems, and software applications for providing healthcare content and information and improving communication between healthcare providers, HMOs, medical providers, insurance companies, and the like and clients via wireless devices.

2. Related Art

Despite improvements in America's health care system over the last few decades, lingering challenges continue to restrain many consumers from quickly and efficiently accessing health care information and services. Some consumers simply lack the necessary communication tools to gain quick and efficient access to health care information and services. Others lack the financial resources and information to speak with health care professionals. In view of these setbacks, consumers, including those with low-incomes, thus often neglect basic health care services for themselves and their families.

Failure to obtain routine examinations prevents health care providers from detecting the early signs of a more serious problem. Health care organizations and insurance providers know all too well the realities of the reduced quality of life attributed to patients who fail to take preventive measures early on. Health care organizations and insurance providers also know all too well the realities of higher medical costs attributed to patients who fail to take preventive measures early on. That is, early and periodic examinations help detect more serious health issues which can ideally be treated to prevent excessive out of pocket costs to the consumer and improve quality of life. In instances where the consumer does not pay for medical assistance, either due to Medicaid or some other subsidy, early detection helps prevent or reduce the likelihood of medical costs being driven up for other consumers in the plan.

Lifeline was established in the 1980s by the federal government to help low-income individuals obtain monthly telephone services for the purpose of finding jobs, accessing health care services, connecting with family, and calling for help in the event of an emergency. Generally the individual must have income at or below a predetermined percentage of the federal poverty guidelines to qualify for Lifeline services. Alternatively, to be eligible, the individual can participate in one of the following federal assistance programs: Medicaid; Supplemental Nutrition Assistance Program (food stamps or SNAP), Supplemental Security Income (SSI), Federal Public Housing Assistance, Low-Income Home Energy Assistance Program (LIHEAP), Temporary Assistance to Needy Families (TANF), National School Lunch Program's Free Lunch Program, Bureau of Indian Affairs General Assistance, Tribally-Administered Temporary Assistance for Needy Families (TTANF), Food Distribution Program on Indian Reservation (FDPIR), Head Start or any State assistance programs.

With changing times, wireless phones have increasingly replaced landline phones as the primary option among consumers/users. For example, Lifeline eligible customers who may be between residences may opt to have a wireless phone on them at all times to ensure not missing an important call from a medical provider or a potential employer. Wireless phone providers have taken the initiative to provide Lifeline eligible users with the assistance they so desperately need under the federal program.

Wireless phone providers have incentivized low-income consumers to sign up and have offered a wireless phone in addition to monthly minutes and/or text messages. For example, prepaid wireless devices and wireless services may include wireless devices having prepaid accounts provided by public, private or governmental agencies (e.g., Lifeline or other U.S., state or local government supported programs for low-income individuals that provide free mobile phone services).

A need exists in the art for innovative methods, systems and software applications to help medical organizations and healthcare providers manage communications with their clients via wireless phones. Another need exists in the art for methods, systems and software applications to determine when a medical organization has contacted a client via a wireless phone to apportion a predetermined rate for this communication. Yet another need exists in the art for methods, systems and software applications to determine when a client has contacted a medical organization via a wireless phone to apportion a predetermined rate for this communication. A further need exists in the art for methods and systems of employing an application on a wireless phone allowing access to a medical organization's website and contact services. Yet a further need exists in the art for methods and systems for securely storing a client's medical information on a wireless phone and/or on a cloud server.

SUMMARY OF THE INVENTION

The foregoing needs are met, to a great extent, by the invention, with a process, system and application for managing communications between medical providers and their clients via wireless phones.

One aspect of the invention is directed to a method for improving communication between a client and healthcare provider, medical provider, healthcare insurance provider, HMO or the like on a wireless device. For brevity, the invention will be described with respect to an HMO. However, the invention is equally applicable to a healthcare provider, medical provider, healthcare insurance provider, or the like. The method includes a step of providing a wireless phone. Next, a communication is displayed from the HMO on a display of the phone. It is determined whether the communication received from the HMO was from a predetermined HMO. A deduction rate is applied to the received communication from the HMO Another aspect of the invention is directed to a system for improving communication between medical providers and their clients. The electronic device includes a non-transitory memory having instructions stored thereon for an application which improves communication between a client and HMO. The system also includes a display for displaying the communication from the HMO. The system further includes a processor that is operatively coupled to the memory and display. The processor is configured to perform instructions including, for example, (i) determining the communication was received from the HMO; and (ii) applying a predetermined deduction rate to the received communication.

Yet another aspect of the invention is directed to a non-transitory computer readable storage medium storing computer-readable instructions for a software application for managing data service on a wireless device, which when executed, causes an electronic device to perform the following steps: (i) display a communication from the HMO on a display of the device; (ii) determine the communication was received by the HMO; and (iii) apply a predetermined deduction rate to the received communication.

There has thus been outlined, rather broadly, certain aspects of the invention in order that the detailed description thereof herein may be better understood, and in order that the present contribution to the art may be better appreciated. There are, of course, additional aspects of the invention that will be described below and which will form the subject matter of the claims appended hereto.

In this respect, before explaining at least one aspect of the invention in detail, it is to be understood that the invention is not limited in its application to the details of construction and to the arrangements of the components set forth in the following description or illustrated in the drawings. The invention is capable of aspects or aspects in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the invention. It is important, therefore, that the claims be regarded as including such equivalent constructions insofar as they do not depart from the spirit and scope of the invention.

BRIEF DESCRIPTION OF THE DRAWINGS

In order to facilitate a fuller understanding of the invention, reference is now made to the accompanying drawings, in which like elements are referenced with like numerals. These drawings should not be construed as limiting the invention and intended only to be illustrative.

DETAILED DESCRIPTION

Figure 1:
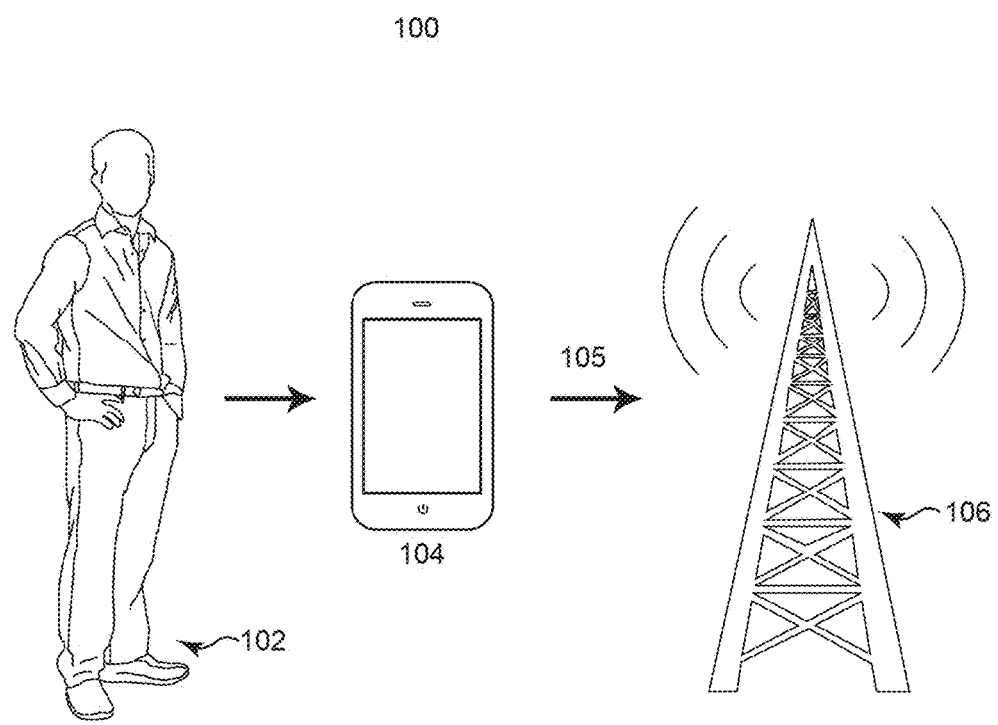
FIG. 1 illustrates an exemplary wireless device system in accordance with an aspect of the invention.

In today's marketplace, Health Maintenance Organizations (HMOs) understand the importance of establishing and maintaining communication pathways with their clients. To advance this initiative, this application presents novel techniques, systems and applications for HMOs to collaborate with wireless service providers. Namely, wireless phones offer various modes of communication, such as, for example, talking on the phone, email, SMS text messaging, and chat options on a portal.

One aspect of the invention is to improve communication between HMOs and their clients via wireless phones. Another aspect of the invention is to improve recognition of HMO communications received by a client via a wireless phone in order to apportion a special deduction rate for the received communications. Yet another aspect of the invention is to improve recognition of client communications that are sent to a HMO via a wireless phone in order to apportion a special deduction rate for the sent communications. A further aspect of the invention is to facilitate open communication and information sharing via an HMO application located on a wireless phone between a client and a HMO. Yet a further aspect of the invention is a method and system for securely storing a client's medical information on the wireless phone and/or on a cloud server.

Reference in this specification to "one aspect," "an aspect," "one or more aspects," "an aspect" or the like means that a particular feature, structure, or characteristic described in connection with the aspect is included in at least one aspect of the disclosure. The appearances of, for example, the phrases "an aspect" in various places in the specification are not necessarily all referring to the same aspect, nor are separate or alternative aspects mutually exclusive of other aspects. Moreover, various features are described which may be exhibited by some aspects and not by the other. Similarly, various requirements are described which may be requirements for some aspects but not by other aspects.

Generally, companies that provide post-paid wireless services are wireless carriers or Mobile Network Operators (MNO) that maintain and control their own wireless networks. Namely, an MNO heavily relies on backend systems to address any provisional, billing, security and data issues that might threaten the health of their networks. On the other hand, a Mobile Virtual Network Operator (MVNO) is a mobile operator that typically does not own its own frequency spectrum or have its own network infrastructure. MVNOs negotiate and enter into business agreements with third party wireless carriers to purchase the right to use their networks for wireless services including volume of data and number of minutes/text messages used. The services provided by the MNOs and MVNOs result in different cellular metering models. The invention is applicable to both MNOs and MVNOs.

It is to be understood that the system modules and method steps described in this application may be employed in various forms of hardware, software, firmware, special purpose processors or a combination thereof. The application preferably is directed to a process and system utilizing a software application including executable code that is operably stored on one or more program storage devices including but not limited to a magnetic floppy disk, RAM, ROM, CD ROM and/or Flash memory.

In aspects including a "wireless network", the network may encompass any type of wireless network from which a Mobile Virtual Network Operator (MVNO) contracts with a Mobile Network Operator (MNO) wireless carrier to provide mobile phone services through the use of an electronic device, such as the Global System for Mobile Communication (GSM) network, Code-Division Multiple Access (CDMA) network, a communication channel as defined herein, or the like, that may utilize the teachings of the present application to allow a wireless device to connect to a wireless network.

In one aspect of the invention, there is described a method for improving user interface with a Health Maintenance Organization (HMO) on a wireless phone operating on a network. Preferably, the cell phone is configured to operate with Lifeline services. The cell phone may have additional software, or is coded to operate under the rules and regulations of the Lifeline services program offered by the federal government.

As will be discussed in more detail below, an HMO is an organization that provides or arranges managed care for health insurance, health care benefit plans, individuals and other entities. In one aspect, the HMOs act as an intermediary between clients, e.g., those seeking medical care, and health care providers, e.g., hospitals, doctors, etc., on a prepaid basis. For clients falling under the income limits of the Lifeline program, they may also be eligible for Medicaid. Medicaid is managed care from HMOs and primary care case management (PCCM).

HMOs generally are incentivized to maintain contact with their clients. Some clients, e.g., those eligible for the Lifeline program, may not have a phone, or access to one, in order to schedule appointments or speak with health care professionals. They also may not have the means to perform research on the World Wide Web regarding the symptoms they're experiencing. In coordination with the Lifeline program, wireless phone providers using the invention establish communication pathways to provide Lifeline eligible clients with improved opportunities to communicate with their HMOs. It is theorized that as more clients seek early screening, detection and prevention of a possibly severe illnesses, the overall cost of health insurance for the general population will drop along with an improvement in quality of life.

FIG. 1 illustrates an electronic device system 100, according to one or more aspects of the present disclosure. The electronic device system 100 may be used to activate, update, or end services on a wireless device 104. The wireless device 104 is preferably a wireless phone. Typically, a user 102 enters the appropriate actions into the wireless device 104. For example, the user may enter an action to update services on the wireless device 104. The actions may include, for example, powering on the already activated wireless device 104. The wireless device 104 communicates over a channel 105 (on a communication channel is defined herein) with a wireless carrier network 106 for services on the wireless device 104.

Figure 2:
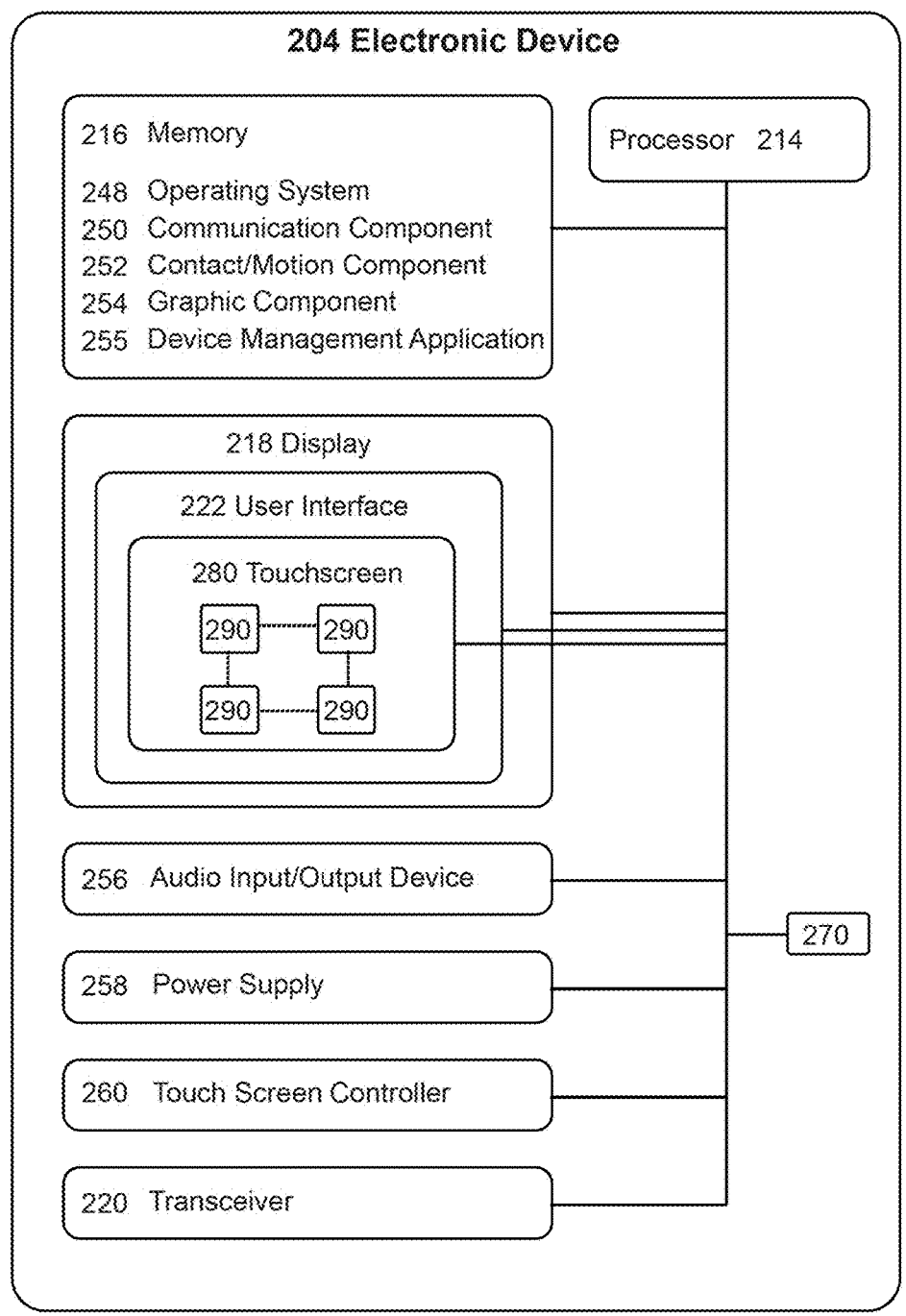
FIG. 2 illustrates an exemplary wireless device in accordance with an aspect of the invention.

In an exemplary aspect, there is provided a wireless phone configured with Lifeline services. FIG. 2 illustrates a wireless device 204, such as, for example, a mobile smart phone which may be employed in many aspects of this application. In an exemplary aspect, the wireless device 204 includes a processor 214, memory 216, display 218 and user interface 222.

The processor 214 may be a central processing unit configured to execute instructions, such as, for example, instructions related to software programs. Any processor can be used for the electronic device as understood by those of ordinary skill in the art. The display 218 may be a liquid crystal display (LCD). Preferably the LCD includes a backlight to illuminate the various color liquid crystals to provide a more colorful display. The user interface 222 may be any type of physical input as readily employed in the field. For example, the user interface may have physical buttons. Alternatively, the user interface may be implemented on a touchscreen 280.

The memory 216 of the wireless device 204 may further include an operating system 248, a communication component 250, a contact/motion component 252, a graphics component 254 and the like. The operating system 248 together with the various components provides software functionality for each of the components of the wireless device 104. The memory 216 may include a high-speed, random-access memory. Also, the memory 216 may be a non-volatile memory, such as magnetic fixed disk storage, flash memory or the like. These various components may be connected through various communication lines including a data bus 270.

The wireless device 104 may include an audio input/output device 256. The audio input/output device 256 may include speakers, speaker outputs, microphones, microphone inputs, and the like, for receiving and sending sound inputs. In an exemplary aspect, the audio input/output device 256 may include an analog to digital converter and a digital to audio converter for audio input and output functions respectively. The wireless device 104 may also include a power supply 258 and a touchscreen controller 260.

In another aspect, the wireless device 104 may include a transceiver 220. The wireless device 104 may provide radio and signal processing as needed to access a network for services. The processor 214 may be configured to process call functions, data transfer, and the like and provide other services to the user.

In an exemplary aspect, the touchscreen 280 of the invention may be implemented in the display 218 and may detect a presence and location of a touch of a user within the display area. For example, touching the display 218 of the wireless device 104 with a finger or hand. The touchscreen 280 may also sense other passive objects, such as a stylus.

In operation, the display 218 may show various objects 290 associated with applications for execution by the processor 214. For example, a user may touch the display 218, particularly the touchscreen 280, to interact with the objects 290. That is, touching an object 290 may execute an application in the processor 214 associated with the object 290 that is stored in memory 216. Additionally or alternatively, touching an object 290 may open a menu of options to be selected by the user. The display 218 may include a plurality of objects 290 for the user to interact with. Moreover the display 218 may include a plurality of screens. The display 218 showing one screen at a time. The user may interact with the display 218 to move a screen into view on the display 218. Various objects 290 may be located in each of the screens.

The touchscreen 280 may have different attributes. The touchscreen 280 may be implemented as a resistive touchscreen, a surface acoustic wave touch screen, a capacitive touch screen, a surface capacitance touchscreen, projected capacitive touch screen, self-capacitance sensors, infrared sensors, dispersive signal technology, acoustic pulse recognition, or the like.

The display 218 is generally configured to display a graphical user interface (GUI) 222 that provides an easy to use visual interface between a user of the wireless device 204 and the operating system or application(s) running on the wireless device 204. Generally, the GUI presents programs, files and operational options with graphical images. During operation, the user may select and activate various graphical images which appear on the display 218 in order to initiate functions and tasks associated therewith.

In another aspect of the invention, the memory 216 of a wireless device 104 includes a database for storing user information. The user information is exemplary, and may include further information as required by the service provider and may include information such as full name, address, date of birth, number, driver's license state and number, email address, contact number, and the like. In one aspect, the database may include security questions. In another aspect, the database may include user specified preferences.

In yet another aspect of the application, the memory 216 of a wireless device 104 includes a device management software application 255. This application 255 allows the user to store confidential data manage settings, functions and confidential information of various applications on their wireless device 204. In an exemplary aspect, the confidential information stored in memory may include personal health information. This information may be accessible by successfully inputting a preset security code. The health information may be sent, upon the user's request, to the HMO. The secure information in the application 255 may also be remotely destroyed. This can be useful if the wireless phone is lost or stolen. In a further aspect, the phone may be configured to automatically destroy all information in the memory upon being de-linked or dropped from the Lifeline program.

In another aspect of the invention, the wireless device 204 displays a communication from the medical provider (HMO) on a display 218. The communication can be any information that is transmitted to the wireless phone from an HMO. In particular, the communication can be an alert of upcoming health news, e.g., flu season precautions and places to obtain shots. Alternatively, the communication can be a message confirming or scheduling a health appointment. In another alternative, the communication includes but is not limited to a bill, medical documents, advice from physicians/nurses, or a response to questions from clients. Alternatively, the communication can be an advertisement from the HMO catered to the individual client.

Figure 3:
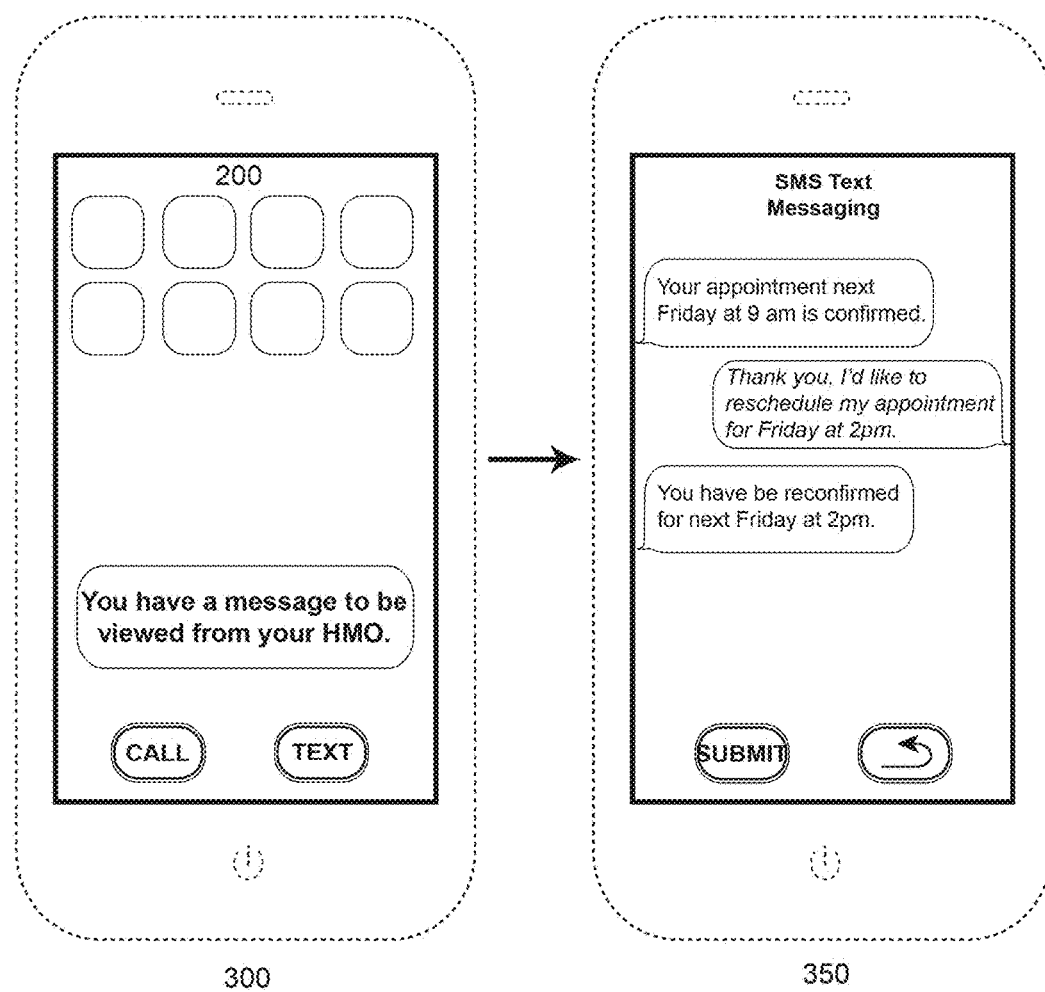
FIG. 3 illustrates an exemplary wireless device having a display of a home screen showing a communication received from a HMO, and a subsequent screen showing a communication received from a HMO and sent to the HMO from the wireless phone in accordance with an aspect of the invention.

As shown in FIG. 3, the HMO has sent a message to the client. In one aspect, the message shows up directly on the display 300 of the wireless device 104. The message states, "You have a message to be viewed from your HMO." A subsequent screen 350 illustrates text messages received from the HMO. The text messages may read, "Your appointment next Friday at 9 am is confirmed." Also shown is a sequential text message that was sent by the client to the HMO. For example, the reply reads, "Thank you, I'd like to reschedule my appointment for Friday at 2 pm." A reply from the HMO, in real-time, may read "You have been reconfirmed for next Friday at 2 pm."

In another exemplary aspect, the phone may require a security code that is enabled on the phone. This is attributed to the transmission of sensitive material over a network. The confidentiality of the material is of utmost importance. The security code can be customized according to preset instructions under federal guidelines, or those set by either the HMO or the wireless service provider. Apart from being at least 4 characters, the code may be made up of all letters, all symbols or combinations thereof. For an additional measure of protection, the code may be case sensitive. In particular, all aspects of the invention should be consistent with HIPAA Privacy Rules that regulate the use and disclosure of Protected Health Information (PHI). In this regard, the transmission of sensitive material may also be encrypted. Encryption may be a symmetric key encryption process or a public key encryption process. For example, in a symmetric-key process, the encryption and decryption keys are the same as is known in the art. Thus communicating parties must have the same key before they can achieve secret communication. In a public-key encryption process, the encryption key is published for anyone to use and encrypt messages. However, only the receiving party has access to the decryption key that enables messages to be read as is known in the art.

Similar to certain security measures mandated for wireless phones working with confidential matters, e.g., government, law and accounting firms, the security code for these Lifeline wireless phones may also require a code which expires after a certain period of inactivity. For example, the phone may prompt the user/client for their security code after 5 minutes of inactivity. In another aspect, the code may need to be input after 30 or minutes of inactivity. In a further aspect, the security code may need to be input after 60 or more minutes of inactivity. As discussed earlier, the duration of inactivity before a security code must be entered is contingent upon the service provider and/or HMO.

In a further aspect, the wireless phone determines whether the communication was received by the HMO. In one aspect, a software application employing an algorithm stored in the memory of the wireless phone determines if the communication was received from the HMO of the user/client. Since there are many HMOs in the marketplace, each wireless device or group of wireless devices is customizable to understand if communications are received from the specific HMO representing the client.

Figure 4:
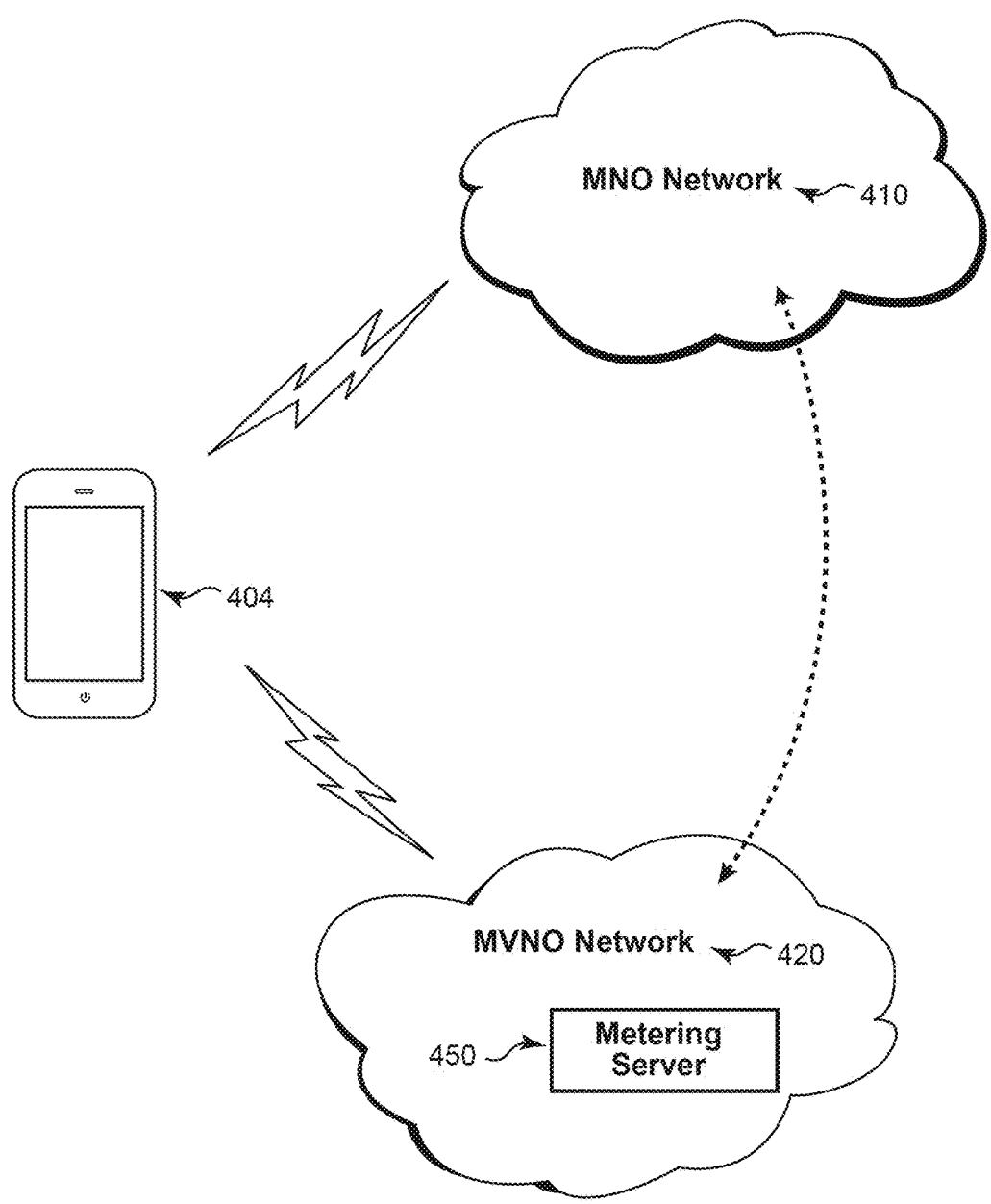
FIG. 4 illustrates an exemplary wireless device connected to a server in accordance with an aspect of the invention.

In another aspect, an external server, either in a MNO or MVNO cloud, is used to determine whether the communication was received by the HMO having a direct relationship with the client. Preferably, this is done in real-time. As illustrated in FIG. 4, the wireless device 404 transmits information to a MNO Network 410 and/or a MVNO Network 420 including a metering server 450. The networks are configured to work together, if necessary.

Even further, after determining that the HMO is affiliated with the client, a predetermined deduction rate is applied to the communication. As discussed above, the communication can be a telephone call that is placed to the client, a text message that is sent to the client, or the like. The communication may also include an email sent to the client. The purpose of the deduction rate is to charge a percentage or portion of the airtime or data usage rate normally applied to the client. Once depleted, the phone is no longer active until additional airtime is added.

In an exemplary aspect, the wireless phone operates on a MVNO network. More preferably, the wireless phone is a pre-paid phone where airtime and data are paid for in advance. For pre-paid phones, the deduction rate may be factored in real-time to ensure a client does not prematurely run out of service. Preferably, metering is performed on the phone to ensure real-time deduction rates.

In an exemplary aspect, the deduction rate is 90%; 80%; 70%; 60%; 50%; 40%; 30%; 20%; 10% and 0% of the normal rate. In one aspect, the deduction rate is 0% meaning the incoming calls, text messages and emails are free. This is an important incentive for clients to use the services offered by the wireless phone. By so doing, early prevention, screening and detection of more serious illnesses are possible.

In a further aspect, it is determined whether an outgoing message, call or email is sent from the wireless phone to the HMO. As explained above, an algorithm determines if the destination address falls within a specific destination path unique to predetermined details of the HMO servicing the user/client. If so, the algorithm tags the outgoing communication with an identifier. In an exemplary aspect, a metering server on a MNO or MVNO cloud determines in real-time whether the outgoing communication was sent to the HMO. If the metering server confirms, then an identifier is placed on the out-going call, SMS text message or email to the HMO provider.

After the determining step, a predetermined deduction rate is applied to the outgoing communication. Similar to the incoming message from the HMO, the outgoing message to the HMO is deducted from the available minutes at a specific rate. The rate can range from 99% to 0% of the normal outgoing rate. In one aspect, the rate is 0%. The rates depend upon the specific wireless server provider and the HMO. In a preferred aspect, the wireless service provider is a MVNO. Moreover, the wireless phone is a pre-paid wireless device meaning airtime and data are paid in advance.

According to yet another aspect of the invention, there is disclosed a mobile-version application of the HMO. The application is stored in memory and displayed on a display of the wireless phone. The application may be a mobile version of the full website accessible via the World Wide Web. The application may come pre-installed on the wireless phone which operates under the Lifeline service program. Moreover, upon receiving an application by a user under the Lifeline service program, the service provider determines who is the user's HMO provider. For example, if the client's HMO provider is based upon Medicaid, a specific application relating thereto would be pre-installed on the wireless phone.

As illustrated in FIG. 3 discussed above, a home screen 200 of the wireless device 204 may include but is not limited to a calling icon, texting icon, and Internet icon allowing a user to perform one or more functions on the wireless device 204. The home screen may also display icons for one or more applications that have been downloaded from the Internet, or retrieved from a store, such as the Google Play, Android market, Apple store, or the like. The user interface 222 of the wireless device 204 displays an application for accessing and managing the client/user's account with the HMO service provider. The application may come pre-installed on the wireless device. Alternatively, the application may be downloaded and installed from an application portal, such as, for example, Google Play, Android market, Apple store, or the like. The application, after being downloaded, may appear on the Home Screen 200 as a shortcut. In an alternative aspect, the application 255 after being downloaded appears on a subsequent screen or in a folder along with plural other applications.

Figure 5:
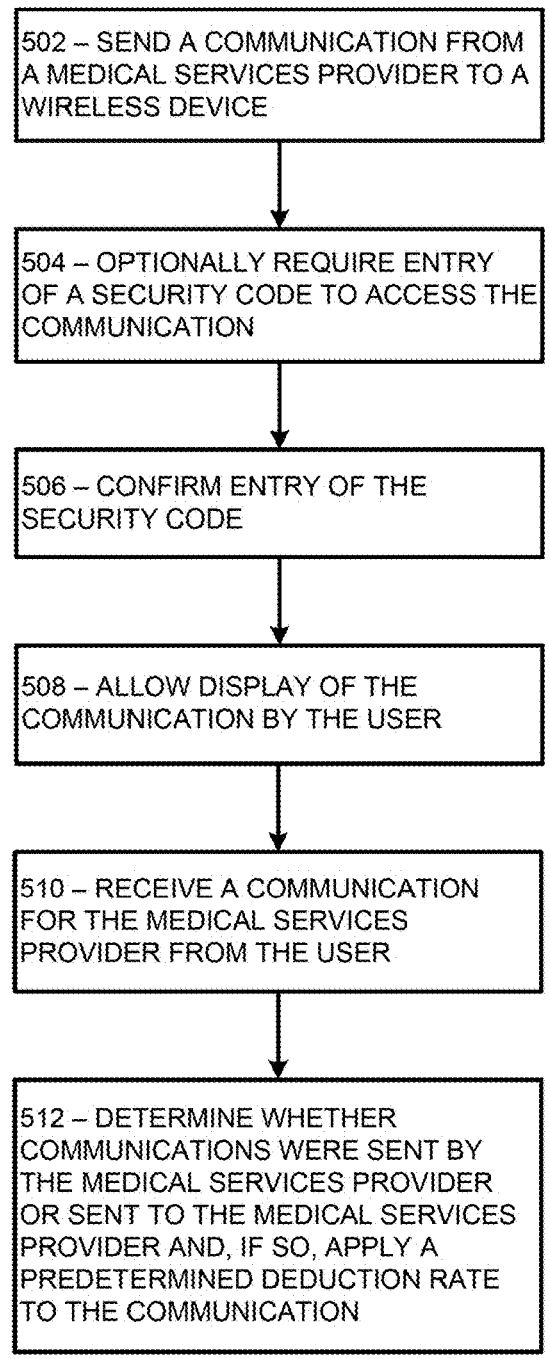
FIG. 5 illustrates an exemplary wireless process in accordance with an aspect of the invention.

FIG. 5 illustrates an exemplary wireless process in accordance with an aspect of the invention. The process shown in FIG. 5 is consistent with the description herein and includes sending a communication from a medical services provider to a wireless device 502. Thereafter, the process may require entry of a security code to access the communication 504. The process may further include confirming entry of the security code by the user 506. Once the security code has been confirmed, the process will allow display of the communication by the user 508. Additionally, the process allows for a communication for the medical services provider be sent from the user and subsequently received by the medical services provider 510. Finally, a determination may be made as to whether the communication was sent by the medical services provider or sent to the medical services provider and, if so, apply a predetermined deduction rate to the communication 512.

Figure 6:
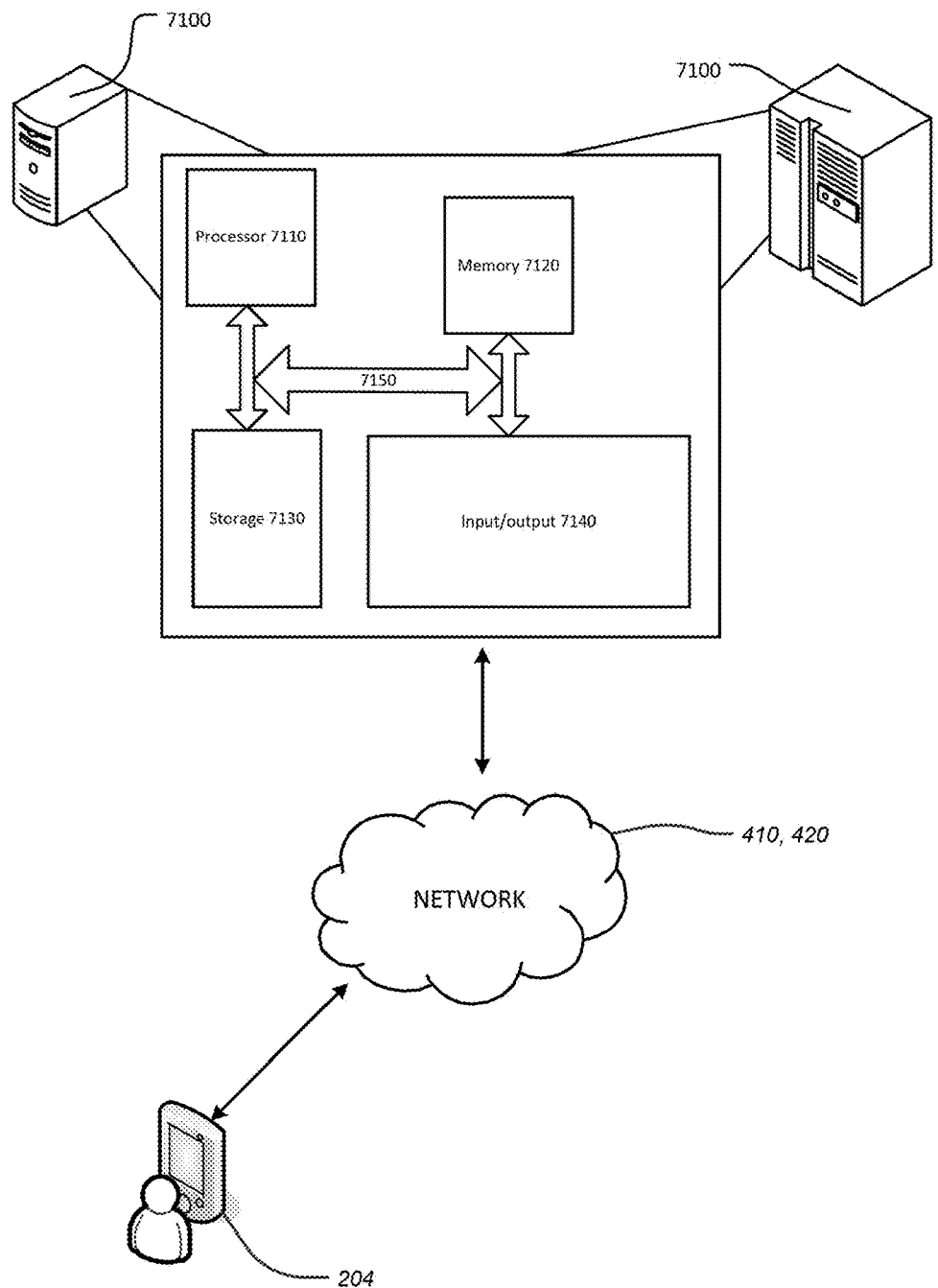
FIG. 6 illustrates an exemplary system in accordance with an aspect of the invention.

FIG. 6 shows a schematic diagram of an exemplary computer system 7100 that can be used to implement a server hosting medical services provider communication. In particular, the computer system 7100 may operate to provide some or all of the medical services provider communication functionality as described herein. The system 7100 includes a processor 7110, a memory 7120, a storage device 7130, and an input/output device 7140. Each of the components 7110, 7120, 7130, and 7140 can, for example, be interconnected using a system bus 7150. The processor 7110 is capable of processing instructions for execution within the system 7100. In one implementation, the processor 7110 is a single-threaded processor. In another implementation, the processor 7110 is a multi-threaded processor. The processor 7110 is capable of processing instructions stored in the memory 7120 or on the storage device 7130 to provide communications to the wireless device 204. In some embodiments, a parallel processing set of systems 7100 connected over a network may be employed, clustered into one or more server centers.

The memory 7120 stores information within the system 7100. In one implementation, the memory 7120 is a computer-readable medium. In one implementation, the memory 7120 is a volatile memory unit. In another implementation, the memory 7120 is a non-volatile memory unit. The storage device 7130 is capable of providing mass storage for the system 7100. In one implementation, the storage device 7130 is a computer-readable medium. In various different implementations, the storage device 7130 can, for example, include a hard disk device, an optical disk device, or some other large capacity storage device. The input/output device 7140 provides input/output operations for the system 7100.

There are many benefits associated with the web version application. Namely, the client may not be required to obtain data services to gain access to the application via their wireless data phone. That is, the application can be accessed at no additional cost to the user. The HMO may have specific arrangements in place with the service providers to offer limited web access to their HMO application.

The application provides easy-to-use services to the client. For example, there is a calendar feature for upcoming appointments. There is an account balance section. There is a summary of services section. Moreover, there is a chat icon through a portal of the application which allows clients to ask questions in real-time to an online HMO representative. The questions can be input using the keypad or graphical user interface. Alternatively, the client can input the question using a talk-to-type feature employing a speaker phone to submit questions or information to the HMO representative.

In yet even another aspect, confidential information of the client may be input into a secure application residing on the wireless phone. The application can be stored in the memory of the device. The application can be secured with a code as discussed above. This application also has a self-terminating feature. This feature is connected to a main server of the phone offering Lifeline services. Specifically, if the phone ceases to be used for Lifeline services or the phone is lost or stolen, an external server is capable of destroying the information. Alternatively, the personal information of the client can be input into the HMO application. The HMO application may come pre-installed on wireless phones received under the Lifeline service program.

In yet a further aspect, the phone comes pre-populated with specific numbers, physical addresses and e-mail addresses of appropriate contact personnel of the HMO. The purpose of this is to ensure the client has all the necessary resources to communicate with the HMO regarding medically-related concerns.

In yet another aspect, the user is permitted to add additional airtime directly from the phone. Namely, if the client uses up the airtime offered under the Lifeline service program, the client is permitted to purchase more minutes through a menu option on their phone. The client can enter a promo code which can be obtained online or from a store. In an alternative aspect, the client can input their debit/credit card information to gain additional talk time.

In yet a further aspect of the invention, there is disclosed a non-transitory computer-readable or processor-readable medium. The terms "computer-readable medium" and "processor-readable medium" include a single medium or multiple media, such as a centralized or distributed database, and/or associated caches and servers that store one or more sets of instructions. The terms "computer-readable medium" and "processor-readable medium" also include any medium that is capable of storing a set of instructions for execution by a processor or that cause a computer system to perform any one or more of the methods or operations disclosed herein.

The non-transitory computer-readable or processor-readable medium includes instructions stored thereon for a software program. In an exemplary aspect, the code or instruction of the software program is executable by a processor of the SIM or electronic device in machine readable form. The code of the application is configured to perform the steps of: (i) providing a wireless phone; (ii) displaying a communication from a HMO on a display of the phone; (iii) determining the communication was received by the HMO; and (iv) applying a predetermined deduction rate to the received communication. The HMO application may also be configured to determine whether a communication was sent from a user via their phone to the HMO. The code may also be configured to apply a predetermined deduction rate to the transmitted communication to the HMO through the phone.

In one or more aspects, the actions and/or events of a method, algorithm or module may reside as one or any combination or set of codes and/or instructions on a computer readable medium or machine readable medium, which may be incorporated into a computer program product. Computer readable storage media includes, but is not limited to, RAM, ROM, EPROM, EEPROM, flash memory or other solid state memory technology, optical storage media, magnetic cassettes, magnetic tape, magnetic disk storage or other magnetic storage devices, or any other physical or material medium which can be used to tangibly store the desired information or data or instructions and which can be accessed by a processor or computing device.

The application may include communication channels that may be any type of wired or wireless electronic communications network, such as, e.g., a wired/wireless local area network (LAN), a wired/wireless personal area network (PAN), a wired/wireless home area network (HAN), a wired/wireless wide area network (WAN), a campus network, a metropolitan network, an enterprise private network, a virtual private network (VPN), an internetwork, a backbone network (BBN), a global area network (GAN), the Internet, an intranet, an extranet, an overlay network, a cellular telephone network, a Personal Communications Service (PCS), using known protocols such as the Global System for Mobile Communications (GSM), CDMA (Code-Division Multiple Access), W-CDMA (Wideband Code-Division Multiple Access), 4G-LTE, Wireless Fidelity (Wi-Fi), Bluetooth, and/or the like, and/or a combination of two or more thereof.

In an embodiment, the invention may be web-based. For example, a server may operate a web application to allow the invention to operate in conjunction with a database. The web application may be hosted in a browser-controlled environment (e.g., a Java applet and/or the like), coded in a browser-supported language (e.g., JavaScript combined with a browser-rendered markup language (e.g., Hyper Text Markup Language (HTML) and/or the like)) and/or the like such that any computer running a common web browser (e.g., Internet Explorer™, Firefox™, Chrome™, Safari™ or the like) may render the application executable. A web-based service may be more beneficial due to the ubiquity of web browsers and the convenience of using a web browser as a client (i.e., thin client). Further, with inherent support for cross-platform compatibility, the web application may be maintained and updated without distributing and installing software on each.

Additionally, the various aspects of the disclosure may be implemented in a non-generic computer implementation. Moreover, the various aspects of the disclosure set forth herein improve the functioning of the system as is apparent from the disclosure hereof. Furthermore, the various aspects of the disclosure involve computer hardware that it specifically programmed to solve the complex problem addressed by the disclosure. Accordingly, the various aspects of the disclosure improve the functioning of the system overall in its specific implementation to perform the process set forth by the disclosure and as defined by the claims.

While the system and method have been described in terms of what are presently considered to be specific aspects, the disclosure need not be limited to the disclosed aspects. It is intended to cover various modifications and similar arrangements included within the spirit and scope of the claims, the scope of which should be accorded the broadest interpretation so as to encompass all such modifications and similar structures. The present disclosure includes any and all aspects of the following claims.

The invention claimed is:

1. A method for improving user access to health services on a wireless device comprising:
   providing the wireless device that includes a processor, a memory, a display, a user interface, and a transceiver, the wireless device being configured to receive and send wireless communications over a wireless network;
   receiving a wireless communication from a health care provider communication system over the wireless network with the transceiver of the wireless device;
   displaying to a user the wireless communication from the health care provider communication system on the display of the wireless device;
   implementing a wireless service metering device in the wireless network:
   determining with the wireless service metering device that the wireless communication was received from the health care provider communication system based on an address of the wireless communication;
   inserting with the wireless service metering device an identifier in the wireless communication received from the health care provider communication system when it is determined that the wireless communication was received from the health care provider communication system based on an address of the wireless communication;

applying with the wireless service metering device a predetermined deduction rate to a wireless service utilized for the received communication from the health care provider communication system based on the identifier in the wireless communication;

transmitting a wireless communication to a health care provider communication system over the wireless network with the transceiver of the wireless device in response to input from the user;

determining with the wireless service metering device that a communication was transmitted from the wireless device to the health care provider communication system based on an address of the wireless communication;

inserting with the wireless service metering device an identifier in the wireless communication transmitted to the health care provider communication system; and applying with the wireless service metering device another predetermined deduction rate to the wireless communication from the wireless device to the health care provider communication system based on the identifier in the wireless communication, wherein the wireless communication transmitted or received with the transceiver of the wireless device over the wireless network comprises at least one of the following: a voice call communication, a SMS message communication, an e-mail message communication, and a pop-up chat communication; and wherein the wireless service metering device comprises one of the following:

the processor of the wireless device implementing an algorithm stored in the memory of the wireless device configured to determine communications transmitted between the wireless device and the health care provider communication system, or a metering server implemented in a mobile virtual network operator cloud configured to determine communications transmitted between the wireless device and the health care provider communication system.

2. The method according to claim 1, further comprising provisioning the wireless device and a wireless service for the wireless device under a Lifeline program, wherein the wireless service metering device comprises the metering server implemented in the mobile virtual network operator cloud configured to determine communications transmitted between the wireless device and the health care provider communication system.

3. The method according to claim 1, wherein the deduction rate calculated by the wireless service metering device is less than 50% of standard airtime rates;

wherein the wireless service metering device deducts an amount of wireless service utilized for the wireless communication from an available amount of wireless service based on the deduction rate; and wherein the wireless service metering device comprises the processor of the wireless device implementing the algorithm stored in the memory of the wireless device configured to determine communications transmitted between the wireless device and the health care provider communication system.

4. The method according to claim 3, wherein the deduction rate calculated by the wireless service metering device is 0%; and wherein the wireless service metering device calculates no deduction from an amount of wireless service utilized for the wireless communication from an available amount of wireless service based on the deduction rate.

5. The method according to claim 1, further comprising:

implementing a health provider service application on the wireless device;

the processor of the wireless device executing the health provider service application;

encrypting with the health provider service application wireless communications to a health care provider communication system; and decrypting with the health provider service application wireless communications from a health care provider communication system, wherein the wireless service metering device comprises the metering server implemented in the mobile virtual network operator cloud configured to determine communications transmitted between the wireless device and the health care provider communication system.

6. The method according to claim 1, further comprising:

implementing a web-accessible health care provider service application on the wireless device; and the processor of the wireless device executing the health provider service application, wherein the health provider service application is configured to communicate consistent with HIPAA Privacy Rules to regulate a use and disclosure of Protected Health Information (PHI);

wherein the health provider service application is configured to implement at least the following: a calendar feature for upcoming appointments, an account balance section, a summary of services section, and a portal configured to communicate text in real-time to an online health provider; and wherein the wireless service metering device comprises the processor of the wireless device implementing the algorithm stored in the memory of the wireless device configured to determine communications transmitted between the wireless device and the health care provider communication system.

7. The method according to claim 6, wherein the deduction rate calculated by the wireless service metering device of the health care provider application is 0%; and wherein the wireless service metering device calculates no deduction from an amount of wireless service utilized for the wireless communication from an available amount of wireless service based on the deduction rate.

8. The method according to claim 1, further comprising:

storing health care provider account information in a secure folder located on the wireless device, wherein the storing of the health care provider account information is stored consistent with HIPAA Privacy Rules to regulate a use and disclosure of Protected Health Information (PHI), and wherein the wireless service metering device comprises the metering server implemented in the mobile virtual network operator cloud configured to determine communications transmitted between the wireless device and the health care provider communication system.

9. The method according to claim 1, further comprising configuring the wireless device, the wireless service, and the wireless service metering device such that the wireless device operates as a pre-paid phone utilizing wireless services based on a prepaid wireless service account, wherein the wireless service metering device comprises the metering server implemented in the mobile virtual network operator cloud configured to determine communications transmitted between the wireless device and the health care provider communication system.

10. The method according to claim 9,
wherein the pre-paid phone operates on a mobile virtual network; and
wherein the wireless service metering device is implemented at least in part in one of the following: the pre-paid phone and the mobile virtual network.

11. A system for improving communication between a user and a health care provider on a wireless device comprising:
a non-transitory memory having instructions stored thereon to provide communication between the user and the health care provider through a health care provider communication system;
the wireless device including a processor, a memory, a display, a user interface, and a transceiver, the wireless device being configured to receive and send wireless communications over a wireless network;
the wireless device configured to receive a wireless communication from a health care provider communication system over the wireless network with the transceiver of the wireless device;
the display configured to display to a user the wireless communication from the health care provider communication system;
a wireless service metering device configured to be implemented in a wireless network;
the wireless service metering device being configured to perform the instructions including determining that the wireless communication was received from the health care provider communication system based on an address of the wireless communication and inserting an identifier in the wireless communication received from the health care provider communication system;
the wireless service metering device configured to apply a predetermined deduction rate to the received communication from the health care provider communication system based on the identifier in the wireless communication;
the wireless device configured to transmit a wireless communication to a health care provider communication system over the wireless network with the transceiver of the wireless device in response to input from the user;
the wireless service metering device is further configured to determine a communication was transmitted from the wireless device to the health care provider communication system based on an address of the wireless communication and inserting an identifier in the wireless communication transmitted to the health care provider communication system; and
the wireless service metering device is configured to apply another predetermined deduction rate to the transmitted communication from the wireless device to the health care provider communication system based on the identifier in the wireless communication,
wherein the the wireless service metering device comprises one of the following:
the processor of the wireless device implementing an algorithm stored in the memory of the wireless device configured to determine communications transmitted between the wireless device and the health care provider communication system, or
a metering server implemented in a mobile virtual network operator cloud configured to determine communications transmitted between the wireless device and the health care provider communication system.

12. The system according to claim 11,
wherein the wireless device is selected from a smartphone, a tablet, and a personal digital assistant;
wherein the wireless service metering device deducts an amount of wireless service utilized for the wireless communication from an available amount of wireless service based on the deduction rate; and
wherein the wireless service metering device comprises the metering server implemented in the mobile virtual network operator cloud configured to determine communications transmitted between the wireless device and the health care provider communication system.

13. The system according to claim 12,
wherein the smartphone is a pre-paid phone with wireless network services provided by a mobile virtual network operator; and
wherein the wireless device and a wireless service for the wireless device is provisioned under a Lifeline program.

14. The system according to claim 11,
wherein the memory includes a web-accessible health care provider application displayed on the display;
wherein the processor of the wireless device is configured to execute the web-accessible health provider service application;
wherein the web-accessible health provider service application is configured to communicate consistent with HIPAA Privacy Rules to regulate a use and disclosure of Protected Health Information (PHI);
wherein the web-accessible health provider service application is configured to implement at least one of the following: a calendar feature for upcoming appointments, an account balance section, a summary of services section, and a portal configured to communicate text in real-time to an online health provider; and
wherein the wireless service metering device comprises the metering server implemented in the mobile virtual network operator cloud configured to determine communications transmitted between the wireless device and the health care provider communication system.

15. The system according to claim 11,
wherein the wireless service metering device is configured to deduct less than 50% of standard airtime rates for the wireless communication;
wherein the wireless service metering device deducts an amount of wireless service utilized for the wireless communication from an available amount of wireless service based on the deduction rate; and
wherein the wireless service metering device comprises the processor of the wireless device implementing the algorithm stored in the memory of the wireless device configured to determine communications transmitted between the wireless device and the health care provider communication system.

16. The system according to claim 15,
wherein the wireless service metering device is configured to deduct 0%; and
wherein the wireless service metering device calculates no deduction from an amount of wireless service utilized for the wireless communication from an available amount of wireless service based on the deduction rate.

17. The system according to claim 11,
wherein the memory includes a secure application for storing health care provider account information;

wherein the memory is configured to store the health care provider account information consistent with HIPAA Privacy Rules to regulate a use and disclosure of Protected Health Information (PHI); and wherein the wireless service metering device comprises the metering server implemented in the mobile virtual network operator cloud configured to determine communications transmitted between the wireless device and the health care provider communication system.

18. A non-transitory computer program product embodying instructions to execute a method for improving user access to health services on a wireless device, the non-transitory computer program product being executed on at least one processor and having instructions comprising:

transmitting with a wireless network a communication from a health care provider communication system to a transceiver of the wireless device, the wireless device including a processor, a memory, a display, a user interface, and the transceiver, and the wireless device being configured to display the wireless communication from the health care provider communication system on the display of the wireless device;

determining with a wireless service metering device that the wireless communication was received from the health care provider communication system based on an address of the wireless communication;

inserting with the wireless service metering device an identifier in the wireless communication received from the health care provider communication system;

applying with the wireless service metering device a predetermined deduction rate to a wireless service utilized for the received communication from the health care provider communication system based on the identifier in the wireless communication;

transmitting with a wireless network a communication to a health care provider communication system from the transceiver of the wireless device in response to input from the user;

determining with the wireless service metering device that a communication was transmitted from the wireless device to the health care provider communication system based on an address of the wireless communication;

inserting with the wireless service metering device an identifier in the wireless communication transmitted to the health care provider communication system; and applying with the wireless service metering device another predetermined deduction rate to the wireless communication from the wireless device to the health care provider communication system based on the identifier in the wireless communication, wherein the deduction rate calculated by the wireless service metering device is 0%;

wherein the wireless service metering device calculates no deduction from an amount of wireless service utilized for the wireless communication from an available amount of wireless service based on the deduction rate;

wherein the wireless device, the wireless service, and the wireless service metering device are configured such that the wireless device operates as a pre-paid phone utilizing wireless services based on a prepaid wireless service account;

wherein the wireless communication transmitted or received with the transceiver of the wireless device comprises at least one of the following: a voice call communication, a SMS message communication, an e-mail message communication, and a pop-up chat communication;

wherein the wireless device and a wireless service for the wireless device are provisioned under a lifeline program; and wherein the wireless service metering device comprises one of the following:

the processor of the wireless device implementing an algorithm stored in the memory of the wireless device configured to determine communications transmitted between the wireless device and the health care provider communication system, or a metering server implemented in a mobile virtual network operator cloud configured to determine communications transmitted between the wireless device and the health care provider communication system.

* * * * *